US007772846B2

(12) United States Patent
Roland (10) Patent No.: US 7,772,846 B2
(45) Date of Patent: Aug. 10, 2010

(54) B0 FIELD DRIFT CORRECTION IN A TEMPERATURE MAP GENERATED BY MAGNETIC RESONANCE TOMOGRAPHY

(75) Inventor: Joerg Roland, Hemhofen (DE)

(73) Assignee: Siemens Aktiengesellschaft, Munich (DE)

( * ) Notice: Subject to any disclaimer, the term of this patent is extended or adjusted under 35 U.S.C. 154(b) by 126 days.

(21) Appl. No.: 12/249,034

(22) Filed: Oct. 10, 2008

(65) Prior Publication Data
US 2009/0096450 A1 Apr. 16, 2009

(30) Foreign Application Priority Data
Oct. 12, 2007 (DE) .................. 10 2007 048 970

(51) Int. Cl.
*G01V 3/00* (2006.01)
(52) U.S. Cl. ...................... 324/309; 324/307
(58) Field of Classification Search ......... 324/300–322; 600/407–445
See application file for complete search history.

(56) References Cited

U.S. PATENT DOCUMENTS

| | | | |
|---|---|---|---|
| 6,462,543 B2 * | 10/2002 | Pittaluga et al. ............. | 324/308 |
| 7,081,752 B2 | 7/2006 | Skloss et al. | |
| 7,323,876 B2 * | 1/2008 | Den Boef ..................... | 324/322 |
| 2008/0287773 A1 * | 11/2008 | Harvey et al. ................ | 600/412 |
| 2009/0238429 A1 * | 9/2009 | Roland et al. ................ | 382/131 |

OTHER PUBLICATIONS

"Noninvasive MRI Thermometry with the Proton Resonance Frequency (PRF) Method: In Vivo Results in Human Muscle," Poorter et al., Magnetic Resonance in Medicine, vol. 32 (1995) pp. 74-81.
"Ex Vivo Tissue-type Independence in Proton-Resonance Frequency Shift MR Thermometry," Peters et al., Magnetic Resonance in Medicine, vol. 40 (1998), pp. 454-459.
"Comparison of Four Magnetic Resonance Methods for Mapping small Temperature Changes," Wlodarczyk et al., Phys. Med. Biol., vol. 44 (1999), pp. 607-624.

* cited by examiner

*Primary Examiner*—Brij B Shrivastav
(74) *Attorney, Agent, or Firm*—Schiff Hardin LLP (57) ABSTRACT

In a method to correct a B0 field drift in a temperature map exposure obtained by magnetic resonance tomography as well as a device to implement such a method, a magnetic resonance phantom is placed at a stored, marked reference position relative to an acquisition coil. A first reference phase image of the phantom is automatically acquired in the acquisition of a first phase image of an examination subject in the unheated state. A second reference phase image of the phantom is automatically acquired in the acquisition of a later second phase image of the examination subject. The phase images are adapted to one another according to the requirements of a calibration of the associated reference phase images.

19 Claims, 4 Drawing Sheets

B0 FIELD DRIFT CORRECTION IN A TEMPERATURE MAP GENERATED BY MAGNETIC RESONANCE TOMOGRAPHY

BACKGROUND OF THE INVENTION

1. Field of the Invention

This invention concerns a method for correcting a B0 field drift in a temperature map exposure produced by means of magnetic resonance tomography. The invention furthermore concerns a device to implement such a method.

2. Description of the Prior Art

An image representation of an examination subject (in particular of a patient body) that graphically reproduces a spatial distribution of the temperature or of a temperature difference within the examination subject is designated as a temperature map. Such a temperature map can be acquired by magnetic resonance (MR) tomography by interaction of the patient with an MR scanner. The presentation of temperature maps that show the temporal change of the temperature distribution within a patient body is a central component of a successful implementation of a tumor ablation in interventional radiology. In order to kill the tumor tissue, the tumor to be removed is heated non-invasively by the application of focused ultrasound, or by the application of laser light or radio waves by means of a probe inserted into the patient body.

In order to be able to continuously monitor the temperature in the patient body during the intervention, the intervention typically occurs either directly in the MR scanner or in immediate proximity to the same. The temperature monitoring ensues by generating temperature maps of the patient body continuously or at regular intervals over a longer time span, typically of 30 to 120 minutes.

For the non-invasive temperature determination by means of magnetic resonance tomography, use is made of the physical effect that the nuclear magnetic resonance frequency of the hydrogen atoms (protons) in water molecules (in particular in the water molecules of the patient body) exhibits a characteristic temperature dependency. As a result of this temperature dependency, temperature differences in the patient body manifest themselves in a spatial variation of the phase of the magnetic resonance signal (represented in the form of complex numbers). Information about the temperature distribution in the patient body at the point in time of acquisition thus can be acquired from an image known as a phase image that reproduces this phase with spatial resolution. Phase images that were acquired at points in time to be compared are typically subtracted from one another on a pixel-by-pixel or voxel-by-voxel basis to determine the (spatially resolved) temperature difference in the patient body between different acquisition points in time. In interventional radiology, a "heated" phase image—i.e. a phase image acquired at a point in time during the intervention—is subtracted from an "unheated" phase image acquired before beginning the intervention. The temperature difference between the two acquisition points in time is then calculated for each pixel from the resulting difference image.

The precision of a temperature map generated in such a manner, in particular the precision with which the temperature difference between two acquisition points in time can be determined from such a temperature map at a specific location of the patient body, is typically impaired by a phenomenon known as the B0 field drift. This is a slow variation of the basic magnetic field (B0 field) of the MR scanner used to generate the temperature map.

A variation of the B0 field also disadvantageously leads to a change of the proton resonance frequency to which the acquisition of a temperature map is tied (in terms of measurement). Like temperature changes in the patient body, variations of the B0 field thus directly affect the phase images, so temperature-dependent phase changes and B0 field-dependent phase changes cannot be differentiated without further measures. An error in the resulting temperature map that normally grows with increasing distance between the acquisition points in time results due to the B0 drift.

The conventional approach to correct the influence of the B0 field drift in the temperature maps, is to select as correction regions spatial regions of the phase images to be compared in which no temperature change is expected between the acquisition points in time.

For B0 drift correction, the correction regions are calibrated to one another in the phase images to be compared. In other words, a phase image to be compared (normally the phase image acquired later) is corrected such that the correction region of the corrected phase image coincides in terms of the phase values with the correction region of the comparison image.

To achieve such a correction region, for the most part a magnetic resonance phantom filled with water that is placed in the image region of the phase image to be acquired has previously been used. Alternatively, a region of the patient body can also be defined as a correction region in which a heating (or also cooling) between the acquisition points in time can be precluded. The correction regions are in any case to be defined by the user.

Both methods for correcting the influence of the B0 field drift are relatively error-prone. In particular, a displacement of the phantom or—if the correction region was defined in the patient body—a change of the patient position between the acquisition points in time can then lead, as a result of then-incorrect B0 drift correction, to a large error of the resulting temperature map.

An error of the B0 drift correction can additionally result from the fact that nevertheless an unintended temperature change occurs in a correction region between the acquisition points in time. Such errors in particular occur when the correction region was selected in the patient body. The use of a phantom on the one hand often leads to a limited flexibility with regard to the slice selection and/or slice orientation, since the phantom must by necessity be contained in the selected image section.

SUMMARY OF THE INVENTION

An object of the invention is to provide a method for correction of a B0 field drift for a temperature map acquisition by means of magnetic resonance tomography, which method is simple to implement and relatively insensitive to errors. A further object of the invention is to provide a device suitable to implement the method.

The above object is achieved according to the invention by a method wherein a magnetic resonance phantom is placed at a stored, marked reference position relative to an acquisition coil of a magnetic resonance tomograph, and a first reference phase image of the phantom is automatically acquired in the acquisition of a first magnetic resonance tomography phase image of an examination subject is based on the stored reference position. Furthermore, a second reference phase image of the phantom is automatically acquired in the acquisition of a later, second phase image, again based on the stored reference position.

To correct a B0 field drift between the acquisition points in time of the first phase image and second phase image, these phase images are adapted to one another according to the requirements of a calibration of the associated reference phase images.

The invention is based on the recognition that the tendency of conventional correction methods toward error is primarily due to the fact that the aforementioned correction regions must be manually selected in the image section of the acquired phase images. Based on this realization is the insight that the tendency of such a correction method toward error can be significantly improved when this selection step is automated in a more reliable manner.

This is achieved by the magnetic resonance phantom being used for correction, the phantom being located outside of the examination subject and thus remains (with good certainty) unaffected by temperature variations in the examination subject. Moreover this automation is achieved by a stored and marked reference position for the phantom being produced that can be located by a device automatically implementing the correction, without requiring interaction with a human user for this purpose.

"Storage" of the reference position means that the location of the reference position is known to a device automatically implementing the method, without human interaction in connection with the method implementation. This storage in particular ensues by storing coordinates that characterize the location of the reference position relative to the acquisition coil in a manner accessible to the device.

In contrast to this, "marking" of the reference position some form of marker that marks the reference position in physical space is provided according to the method. In the simplest case, the maker a rough marking (for example formed by color symbols or the like) that enable a user to place the phantom precisely and reproducibly at the provided reference position. In a refined variant of the method, the marking of the reference position ensues by fixing structure that holds the phantom in the reference position. The fixing structure can be formed by a retainer that holds the phantom relative to the reference position such that the phantom still can be removed. As an alternative, the phantom is permanently fixed in the reference position by a suitable structure.

In a comparably simple embodiment of the invention, the acquisition coil relative to which the reference position is defined is the image acquisition coil that is provided to acquire the raw data of the examination subject. In this case, both the phase images of the examination subject and the respective reference phase images of the phantom are generated from raw data of one and the same acquisition coil. In an alternative embodiment of the invention, different acquisition coils—namely an image acquisition coil and a reference acquisition coil separate from this—are provided to acquire the phase images of the examination subject and to acquire the reference phase images of the phantom. In this case, the reference position of the phantom is defined relative to the reference coil. The acquisition coil associated with the phantom, in particular the possibly provided reference acquisition coil, is also used as a transmission coil, i.e. also used to excite the hydrogen atoms of the phantom.

The differentiated embodiment of the invention with two separate acquisition coils to acquire the phase images of the examination subject, or to acquire the reference phase images of the phantom in particular, has the advantage that the phantom for acquisition of the reference phase images can be placed in the MR scanner independent of the image acquisition coil. When the reference acquisition coil is also used as a transmission coil, the phantom and the reference acquisition coil can be arranged at an arbitrary location within the measurement region (field of view—FOV) of the magnetic resonance scanner. Given the use of a separate reference acquisition coil, it is not necessary to conduct a location selection in the acquisition of the reference phase images by the application of a suitable magnetic gradient field. Therefore, only very little measurement time is required for the acquisition of a reference phase image. The correction method thus can be implemented with a time saving.

Particularly with a shared acquisition coil for acquisition of phase images and reference phase images, the phantom is advantageously fashioned annularly, with the diameter of the phantom being advantageously adapted to the diameter of the acquisition coil. Such a phantom can be arranged particularly well in the acquisition region of the acquisition coil without hindering the positioning of the acquisition coil with regard to the patient.

The reference position is preferably defined such that the phantom is arranged directly at (i.e. in immediate proximity to) the acquisition coil.

In a further embodiment of the invention, containers filled with fat and/or oil are used as a phantom. The physical effect observed to detect the temperature change, namely the shift of the proton resonance frequency, visibly occurs only with water molecules. In contrast, temperature changes in fat or oil have no significant effect on the phase images. Given use of a fat/oil phantom, a precise correction of the B0 field drift is therefore possible even for the case that the temperature of the phantom changes between the acquisition points in time. The use of a fat/oil phantom for B0 drift correction is therefore inventive by itself.

The device according to the invention has a marker for marking a reference position for a magnetic resonance phantom relative to an acquisition coil. The device furthermore has a control unit that is fashioned to automatically prompt the acquisition of an associated reference phase image of the phantom given the acquisition of a phase image of an examination subject. The device also has a correction unit that is fashioned to adapt two phase images acquired at different times to one another according to the requirements of a calibration of two reference phase images respectively associated with the phase images.

In the simplest embodiment, the device is provided as a retrofit package for an existing conventional magnetic resonance tomography apparatus, and in this embodiment has only those items that are not already components of the magnetic resonance tomography apparatus. For example, the device to implement the method can normally resort to the acquisition coil of the magnetic resonance scanner that is conventionally present already, as long as placement of the phantom (possibly also already present) in the defined reference position relative to the acquisition coil is achieved by the marker. The acquisition coil and the phantom are therefore not necessarily components of the correction device. Nevertheless, a special acquisition coil and/or a special phantom could naturally be provided as additional components of the correction device. In the case of a retrofit package, the control unit and/or the correction unit preferably are software modules that modify, replace or supplement the conventional control software of the magnetic resonance tomography apparatus, in particular in the context of software update or plug-in.

As an alternative, the device according to the invention can already be integrated into a magnetic resonance tomography apparatus or its components (for example a head coil or breast coil).

If, as described above, the device includes a separate reference acquisition coil for acquisition of raw data for reference phase images, this reference acquisition coil is preferably combined with an image acquisition coil into a permanently connected module. In addition or as an alternative, the phantom is integrated with the associated acquisition coil (i.e. with the reference acquisition coil, in the event that one is present) or otherwise with the image acquisition coil into a permanently connected module. The integral combination of the phantom with the image acquisition coil, or the reference acquisition coil, is particularly user-friendly since the user does not necessarily have to come into contact with the B0 drift correction. This design of the device therefore also enables a particularly foolproof implementation of the correction method.

DESCRIPTION OF THE PREFERRED EMBODIMENTS

Figure 1:
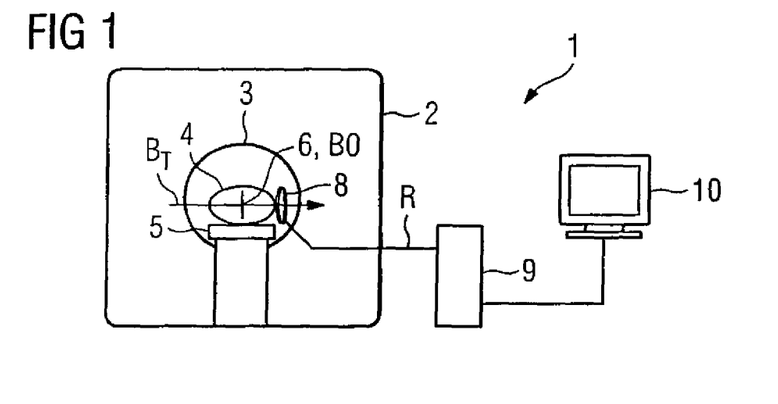
FIG. 1 schematically illustrates a magnetic resonance tomography apparatus with a device to correct a B0 field drift in a temperature map exposure.

The magnetic resonance tomography apparatus 1 shown in FIG. 1 has a scanner 2 with a tunnel or bore 3 therein into which a patient body 4 can be inserted as an examination subject for the purpose of image data acquisition. A patient table 5 is provided to support the patient body 4.

Figure 2:
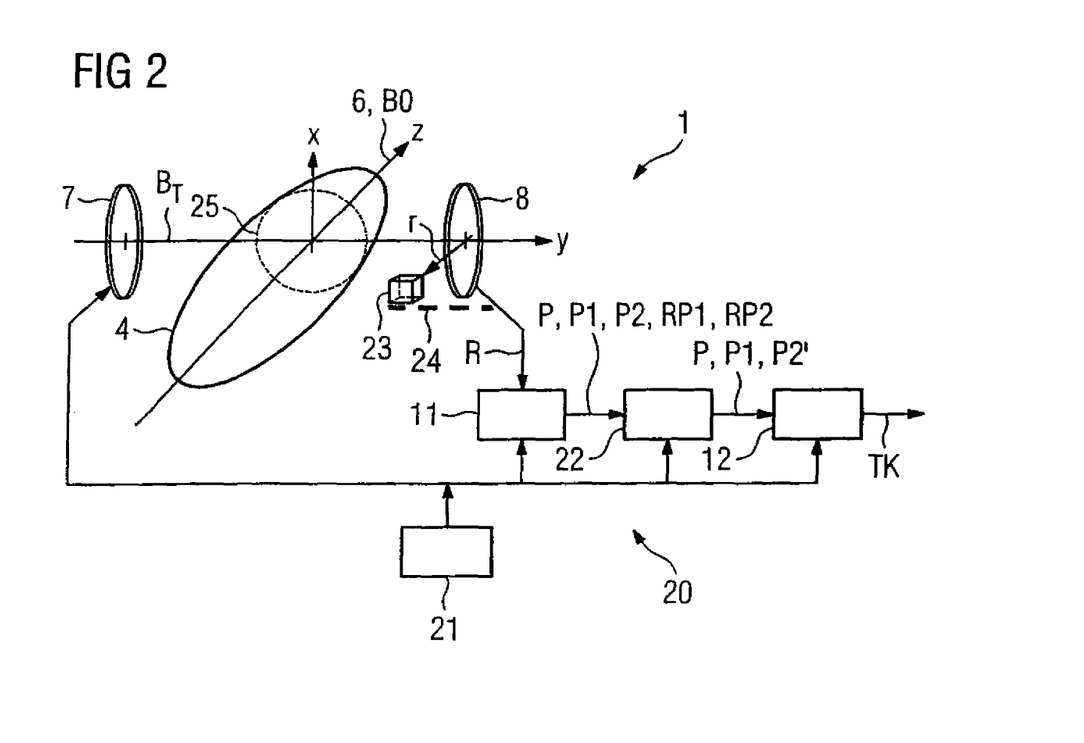
FIG. 2 schematically illustrates the examination subject and a first embodiment of the correction device.

The scanner 2 contains (is not shown) magnetic coils with which a basic magnetic field B0 aligned parallel to a tunnel axis 6 is generated in the tunnel 3. The direction predetermined by the tunnel axis 6 is subsequently also designated as the z-direction (FIG. 2).

The scanner 2 furthermore contains gradient coils by means of which one or more magnetic gradient fields can be superimposed on the constant basic magnetic field B0. The magnetic field strength of each gradient field decreases or increases in a defined manner in the z-direction and/or perpendicular thereto (x-direction, y-direction). A specific spatial region within the patient body 4 is able to be selected by means of these gradient fields.

The scanner 2 also has a transmission coil 7 (FIG. 2) for generation of a radio-frequency alternating magnetic field $B_T$ transverse to the basic magnetic field B0, with which alternating magnetic field $B_T$ hydrogen nuclei in the patient body 4 can be magnetically excited.

The excitation of the hydrogen nuclei results in a fluctuating magnetization that can be measured in the form of an electrical signal by means of an (image) acquisition coil 8. Raw data R are derived from this signal.

A tomogram T, i.e. a three-dimensional image of the patient body 4 or of a part of said patient body 4, is derived from the raw data R by numerical-mathematical calculation by evaluation logic of the magnetic resonance tomography apparatus 1 that is implemented in a computerized control and evaluation system 9. The tomogram T can be presented on a monitor 10 of the magnetic resonance tomography apparatus 1 (for example in the form of two-dimensional slices).

The magnetic resonance tomography apparatus 1 also has typical input means (such as keyboard, mouse etc.) for control.

For the image data acquisition, the gradient coil and the transmission coil 7 of the magnetic resonance tomography apparatus 1 are suitably controlled by a control program implemented in the control and evaluation system 9 so that various spatial regions of the patient body 4 are selectively chosen and excited in the manner of a grid. The respectively generated magnetization is read out via the acquisition coil 8.

As described above, the generation of a temperature map TK of the patient body 4 is based on the acquisition of phase images P of the patient body 4. Such a phase image P contains the phase of the aliased magnetic resonance signal that is present with spatial resolution in the form of complex numbers. The magnetic resonance tomography apparatus 1 a phase image generation unit 11 (FIG. 2) to generate phase images P from the raw data R. For simplification, all hardware and software components that are required for numerical calculation of the raw data R, for calculation of the spatially-resolved phase of the calculation signal and for generation of the phase images P from the calculated phase values are encompassed by the term "phase image generation unit 11".

The generate a temperature map TK from the phase images P of the patient body 4, the magnetic resonance tomography apparatus 1 furthermore has a temperature map generation unit 12 (FIG. 2). This unit is a software module that is a component of the evaluation logic implemented in the control and evaluation system 9.

In addition to the components described above, the magnetic resonance tomography apparatus 1 according to FIG. 2 has a drift correction device 20 corrects a drift of the basic magnetic field B0 during the temperature map acquisition. The device 20 includes a control unit 21, a correction unit 22, a magnetic resonance phantom 23 as well as a mount 24 (only schematically indicated here) for the phantom 23. The device 20 otherwise uses the components of the magnetic resonance tomography apparatus 1, in particular the acquisition coil 8, the gradient coil and the transmission coil 7, as well as the phase image generation unit 11 and the temperature map generation unit 12.

The control unit 21 is a software module that represents a component of the control program implemented in the control and evaluation system 9. The control unit 21 hereby suitably controls the transmission coil 7, the phase image generation unit 11, the correction unit 22, the temperature map generation unit 12 and, if applicable, the gradient coil, and thus effects the automatic implementation of the method described in detail below.

The correction unit 22 is an additional software module that forms a component of the evaluation logic of the control and evaluation system 9. The correction unit 22 implements the calculations required for the correction method (described in detail in the following) on the basis of the phase images P supplied by the phase image generation unit 11.

The magnetic resonance phantom 23 is a container (merely shown here as an example in the shape of a cube) that is filled with a fat or an oil.

The mount 24 is fashioned such that it permanently or removable holds the phantom 23 in a defined reference position r relative to the acquisition coil 8. The coordinates of the reference position r are stored in the control unit 21.

To acquire the temperature map TK (FIG. 6) of the patient body 4 with accompanying correction of a possible drift of the basic magnetic field B0, it is first ensured (if it is the case that the phantom 23 can be removed from the mount 24) that the phantom 23 is currently placed in the mount 24 at the provided reference position r. This step is naturally omitted if the phantom 23 is permanently fixed to the acquisition coil 8 by the mount 24.

The control unit 21 subsequently initiates the acquisition of a first phase image P1 of a region 25 of the patient body 4 to be acquired (FIG. 3) at a point in time t0 by activation of the transmission coil 7 and the gradient coil, as well as via activation of the phase image generation unit 11. This phase image P1 documents an initial state in comparison to which the later temperature development should be determined.

In order to enable the correction of the B0 field drift, the control unit 21 initiates the acquisition of an associated reference phase image RP1 (FIG. 3) of the phantom 23 in connection with the acquisition of this first phase image P1—thus simultaneously, immediately before or immediately after the acquisition of said first phase image P1.

In the embodiment of the device 20 according to FIG. 2, the same acquisition coil 8 with which the phase image P1 is also acquired is used for this purpose. The control unit 21 selects a spatial region corresponding to the phantom 23 in the acquisition field of the acquisition coil 8 via corresponding activation of the gradient coil while resorting to the stored coordinates of the reference position 3, and prompts the phase image generation unit 11 to acquire the reference phase image RP1.

At a later point in time t1, a second phase image P2 of the same selected region 25 of the patient body 4 is generated analogous to the generation of the phase image P1, and a second reference phase image RP2 of the phantom 23 is generated analogous to the generation of the reference phase image RP1.

Figure 3:
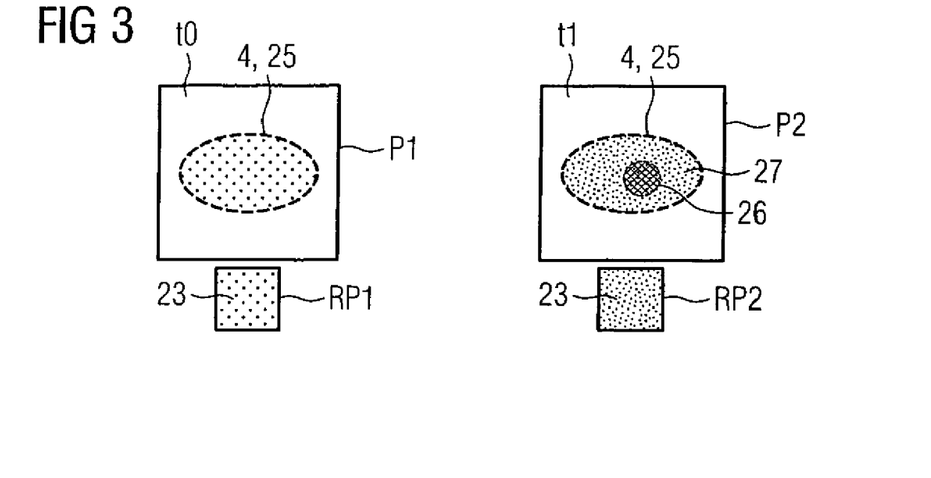
FIGS. 3 through 6 respectively schematically show, corresponding to one another, successive steps of a method implemented by the correction device according to FIG. 2.

As schematically shown in FIG. 3, the phase images P1, P2 and the reference phase images RP1, RP2 exist in terms of data as image data sets separate from one another. As an alternative, however, each phase image P1, P2 can also be combined with the respective associated reference phase image RP1, RP2 into a common image data set. In particular, the phantom 23 can be imaged in a mutual image together with the patient body 4, such that the reference phase image RP1, RP2 can be part of the associated phase image P1 or P2. Since the phase is spatially homogeneous within the phantom 23, the reference images RP1 and RP2 can also respectively consist of only a single pixel, thus a single phase value.

In the scheme according to FIG. 3, in contrast to the earlier phase image P1 the later phase image P2 shows a region 26 of the imagined patient body 4 in which the phase values clearly deviate from the surroundings (indicated by deviating grey values in the representation). This phase difference indicates that the patient body 4 was heated in the region 26 relative to the initial state. In addition to this, however, the unheated regions 27 of the imaged patient body 4 also indicate phase values in the phase image P2 that deviate slightly from the corresponding phase values in phase image P1. For the purposes of the present example, it is assumed that the temperature of these regions 27 between the point in time t0 and the point in time t1 has actually remained unchanged, and that instead the phase change in these regions 27 is to be ascribed exclusively to a drift of the basic magnetic field B0 between the point in time t0 and the point in time t1.

As can be seen from FIG. 3, the phase change caused by the B0 field drift in the "unheated" regions 27 of phase images P1 and P2 is again reflected in the same manner as in the corresponding reference phase images RP1 and RP2. This fact is utilized according to FIG. 4 to correct the influence of the B0 field drift in the phase image P2. For this, the reference phase image RP2 is calibrated on the reference phase image RP1 with regard to the phase values by the correction unit 22, as is indicated by the arrow 28a in FIG. 4. The information of the original reference phase image RP2 is thus modified such that a modified reference phase image RP2' (FIG. 5) resulting from this coincides as much as possible with the reference phase image RP1 in terms of the phase values.

Figure 4:
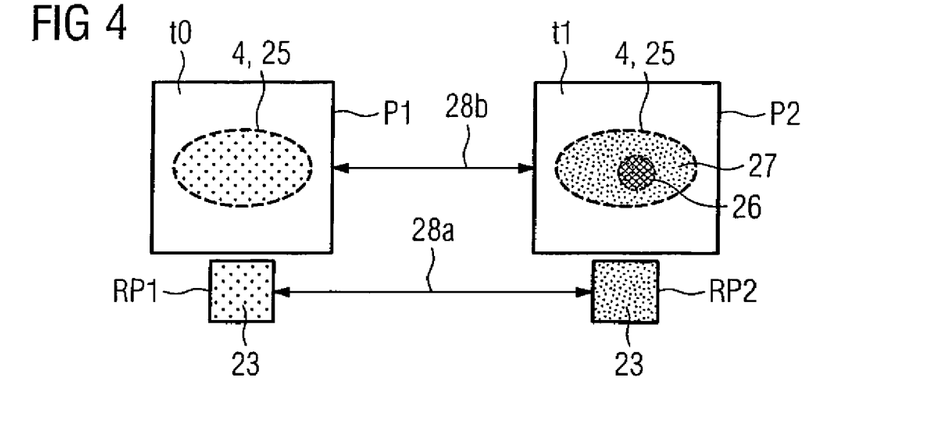

Analogous to the reference phase image RP2, i.e. in the same manner, the phase values of the phase image P2 are also modified by the correction unit 22, whereby the phase difference of the phase images P1 and P2 that is caused by the B0 field drift is compensated (indicated by arrow 28b in FIG. 4).

Figure 5:
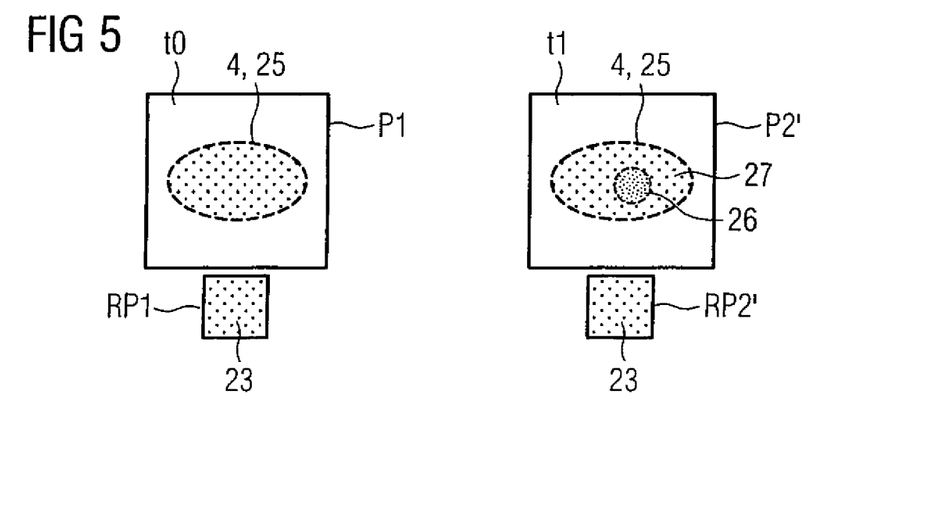

The result of this B0 drift correction is shown in FIG. 5. In particular a corrected phase image P2' derived (in the framework of the correction) from the original phase image P2 and the corresponding corrected reference phase image RP2' are recognizable in FIG. 5. In the further method, the corrected phase image P2' is used instead of the original phase image P2 to produce the temperature map.

Figure 6:
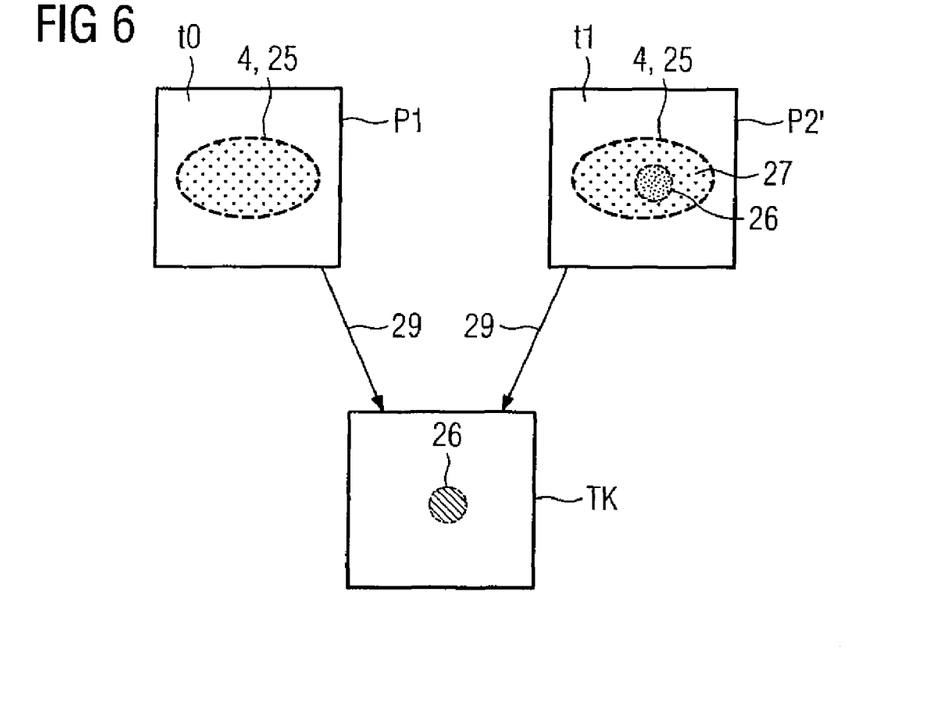

For this purpose, in a final method step according to FIG. 6 a difference image that reflects the spatially-resolved phase difference between the phase images P1 and P2' is generated (indicated by arrows 29) by the temperature map generation unit 12 from the phase image P1 and the corrected phase image P2'. The finished temperature map TK is derived from this difference image by means of a stored characteristic line.

Figure 7:
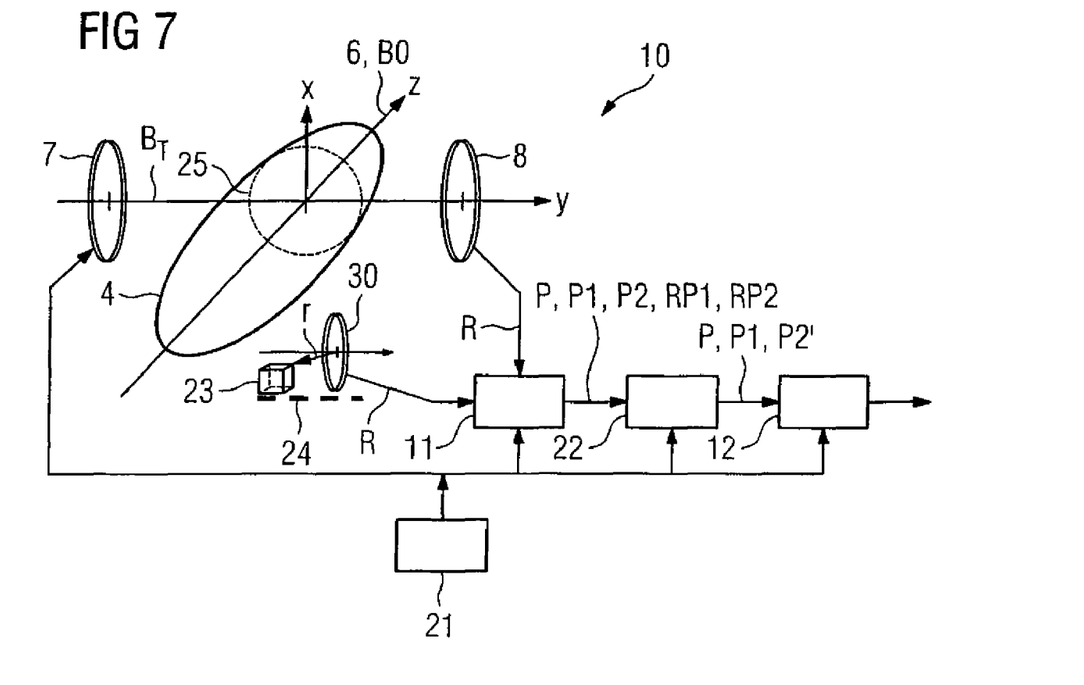
FIG. 7 shows, in representation according to FIG. 2, the examination subject and a second embodiment of the correction device.

FIG. 7 shows a variant of the device 20 in which this comprises a reference acquisition coil 30 separate from the (image) acquisition coil 8 of the magnetic resonance tomograph 1. The image acquisition coil 8 hereby serves exclusively for acquisition of the raw data R for the phase images P1 and P2 of the patient body 4, while the respective associated reference phase images RP1 and RP2 are generated from the raw data R acquired by the reference acquisition coil 30. The reference position r of the phantom 23 is correspondingly defined here relative to the reference acquisition coil 30. The mount 24 is correspondingly attached such that it holds the phantom 23 in this reference position r in the acquisition field of the reference acquisition coil 30.

In the embodiment according to FIG. 7, the image acquisition coil 8 and the reference acquisition coil 30 are units detached from one another, such that the reference acquisition coil 30 and the phantom 23 can be placed at any point within the measurement field (field of view—FOV) of the tube 2. The reference acquisition coil 30 is preferably dimensioned significantly smaller than the image acquisition coil 8, and in particular approximately adapted to the dimension of the phantom 23. The phantom 23 in this embodiment is also preferably dimensioned small in comparison to typically body dimensions. In a preferred embodiment, a cuboid or cylindrical body with typical dimensions of, for instance, 4 cm is used as a phantom 23.

Figure 8:
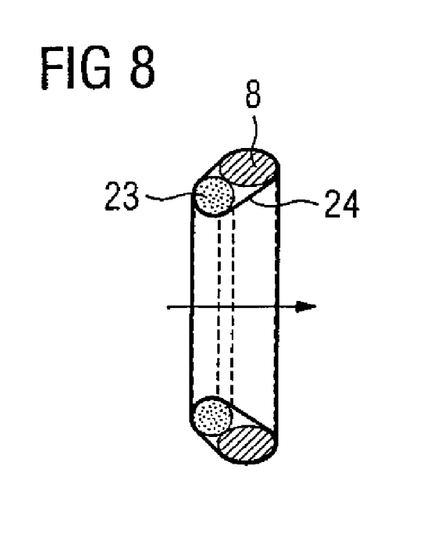
FIG. 8 is a schematic cross-section of an image acquisition coil of the magnetic resonance tomography apparatus with an annular magnetic resonance phantom attached thereto.
Figure 9:
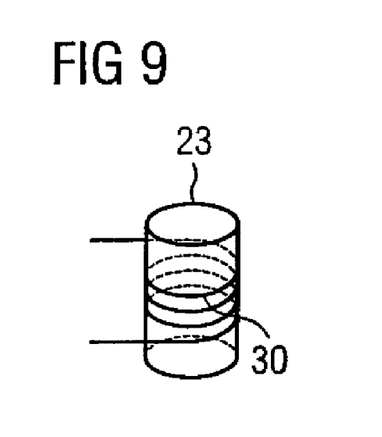
FIG. 9 shows, in representation according to FIG. 8, a reference acquisition coil of the correction device with a phantom incorporated therein.

FIGS. 8 and 9 show specific embodiments of the phantom 23 and of the associated acquisition coil 8 or, respectively, 30 in closer detail.

According to FIG. 8, the phantom 23 is fashioned in the shape of a ring, in particular as an annular tube, and is arranged immediately adjacent to the associated acquisition coil. This embodiment of the phantom 23 is in particular provided for use in the device variant according to FIG. 2. The acquisition coil is therefore in particular the image acquisition coil 8 of the magnetic tomograph 1. The phantom 23 has a diameter significantly corresponding to the acquisition coil 8 and is approximately coaxially fixed relative to the acquisition coil 8. In the simplest case, adhesive tape serves as a mount 24 with which the phantom 23 is fixed to the acquisition coil 8.

FIG. 9 shows a particularly compact and simple realization of the phantom 23 for an application in the device variant according to FIG. 7, together with the associated reference acquisition coil 30. The phantom 23 has an essentially cylindrical shape and is formed by a test tube, for example. The reference acquisition coil 30 is directly wound around the lateral surface of the phantom 23 and, for example, is affixed to the phantom 23 via adhesive tape, adhesive or a sealing compound. The unit thus formed from the phantom 23 and the reference acquisition coil 30 is, for example, placed on the patient table 5 next to the patient body 4 for acquisition of the reference phase images RP1, RP2.

Figure 10:
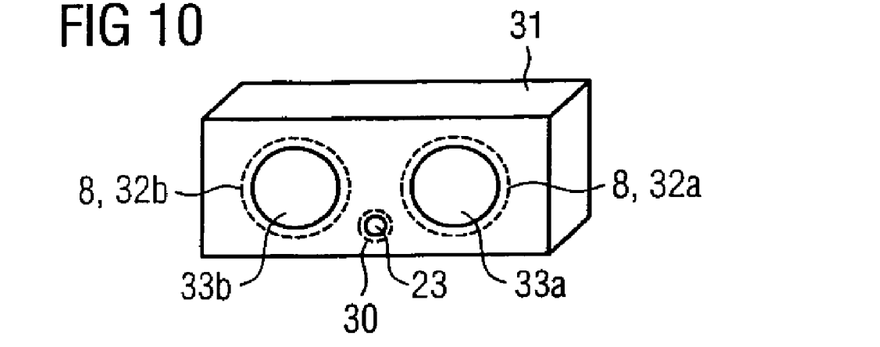
FIG. 10 schematically illustrates an integrated module with an image acquisition coil fashioned as a breast coil, a reference acquisition coil and a phantom incorporated into the reference acquisition coil.

According to FIG. 10, the image acquisition coil 8 and the reference acquisition coil 30 are combined into an integrated unit in a common housing 31 with the phantom 23 incorporated therein according to FIG. 9. The image acquisition coil 8 is hereby fashioned as a breast coil and comprises two sub-coils 32a, 32b, of which each respectively surrounds a housing recess 33a, 33b provided to accommodate a breast. The reference acquisition coil 30 is arranged between the housing recesses 33a 33b together with the phantom 23 incorporated therein. The integrated execution of the acquisition coils 8 and 30 as well as of the phantom 23 according to FIG. 10 in particular has the advantage that the device components required for correction of the B0 field drift are not visible to the user. In this case the correction of the B0 field drift occurs without the user even having to care in the slightest. The generation of a temperature map using the correction method described in the preceding for the B0 field drift is therefore also foolproof to the highest degree.

Deviating from the embodiments of the invention described in connection with FIGS. 7, 9 and 10, in an additional embodiment of the invention (not explicitly shown) the reference acquisition coil 30 is fashioned as a combined transmission/reception coil, wherein in this case the excitation of the phantom 23 for the acquisition of the reference phase images RP1, RP2 ensues not via the transmission coil 7 but rather with the reference acquisition coil 30. A spatial selection via activation of the gradient coil is in this case not required to acquire the reference phase images RP1, RP2. The image acquisition coil 8 can also be fashioned as a combined transmission/reception coil. In this case, the separate transmission coil 7 can be entirely omitted.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for correcting a B0 field drift in a temperature map exposure obtained by magnetic resonance tomography, comprising the steps of:
    placing a magnetic resonance phantom at a stored, marked reference position relative to a magnetic resonance acquisition coil;
    contemporaneously with acquisition of magnetic resonance data from an examination subject in an unheated state representing a first phase image, automatically acquiring magnetic resonance data from the phantom representing a first reference phase image;
    contemporaneously with acquisition of magnetic resonance data from the examination subject at a time subsequent to acquisition of said first reference phase image, automatically acquiring magnetic resonance data from the phantom representing a second reference phase image; and
    identifying adaptations necessary to calibrate said first and second reference phase images relative to each other, and adapting said first and second phase images relative to each other according to said adaptations.

2. A method as claimed in claim 1 comprising marking said reference position by a fixing structure that fixes said phantom in said reference position.

3. A method as claimed in claim 1 comprising employing an image data acquisition coil to acquire said magnetic resonance data representing each of said first phase image and said second phase image, and employing a reference data acquisition coil, separate from said image data acquisition coil, to acquire said magnetic resonance data from said phantom representing said first and second reference phase images, and placing said magnetic resonance phantom in said stored, marked reference position relative to said reference data acquisition coil.

4. A method as claimed in claim 1 comprising transmitting radio frequency signals into the examination subject and the phantom in order to excite nuclei to produce said magnetic resonance data representing said first and second phase images and said magnetic resonance data representing said first and second reference phase images, and using said acquisition coil as a transmission coil to transmit said radio frequency signals.

5. A method as claimed in claim 1 comprising employing an annular phantom as said magnetic resonance phantom.

6. A method as claimed in claim 5 wherein said acquisition coil has a diameter, and comprising employing an annular phantom having a diameter adapted to said diameter of said acquisition coil.

7. A method as claimed in claim 1 comprising attachments of magnetic resonance phantom directly to said acquisition coil.

8. A method as claimed in claim 1 comprising employing a container filled with a material selected from the group consisting of fat and oil as said magnetic resonance phantom.

9. A device for correcting a B0 field drift in a temperature map exposure obtained by magnetic resonance tomography, comprising:
    a magnetic resonance scanner having a magnetic resonance acquisition coil;
    a magnetic resonance phantom placed at a stored, marked reference position relative to said magnetic resonance acquisition coil;
    a controller that operates said magnetic resonance scanner to acquire, contemporaneously with acquisition of magnetic resonance data from an examination subject in an unheated state representing a first phase image, magnetic resonance data from the phantom representing a first reference phase image;
    said controller also operating said magnetic resonance scanner to acquire, contemporaneously with acquisition of magnetic resonance data from the examination subject at a time subsequent to acquisition of said first reference phase image, magnetic resonance data from the phantom representing a second reference phase image; and a computer configured to identify adaptations necessary to calibrate said first and second reference phase images relative to each other, and to automatically adapt said first and second phase images relative to each other according to said adaptations.

10. A device as claimed in claim 9 wherein said marker comprises a fixing structure that folds said phantom in said reference position.

11. A device as claimed in claim 9 comprising an image data acquisition coil that acquires said magnetic resonance data representing said first and second phase images, and a reference data coil, separate from said image acquisition coil, that acquires said magnetic resonance data representing said first and second reference images.

12. A device as claimed in claim 11 wherein said reference data acquisition coil also serves as a transmission coil for transmitting radio frequency signals that excite nuclei in said phantom to generate said magnetic resonance data representing said first and second reference phase images.

13. A device as claimed in claim 11 wherein said reference data acquisition coil and said image data acquisition coil form a permanent, combined module.

14. A device as claimed in claim 11 wherein said magnetic resonance phantom and said reference data acquisition coil form a permanent, combined module.

15. A device as claimed in claim 9 wherein said magnetic resonance phantom is an annular phantom.

16. A device as claimed in claim 15 wherein said acquisition coil has a diameter, and wherein said annular phantom has a diameter adapted to said diameter of said acquisition coil.

17. A device as claimed in claim 9 wherein said phantom is removably attachable to said acquisition soil.

18. A device as claimed in claim 9 wherein said magnetic resonance phantom comprises a container filled with a material selected from the group consisting of fat and oil.

19. A magnetic resonance tomography apparatus comprising:

a magnetic resonance scanner configured to interact with an examination subject to acquire magnetic resonance data therefrom, said magnetic resonance scanner comprising a basic field magnetic that generates a B0 field exhibiting a B0 field drift, and an acquisition coil that acquires magnetic resonance signals from the examination subject in the scanner;

a magnetic resonance phantom placed at a stored, marked reference position relative to said acquisition coil;

a controller configured to operate said magnetic resonance scanner to acquire magnetic data from the examination subject representing a first phase image and to contemporaneously acquire magnetic resonance data from the phantom representing a first reference phase image;

said controller being configured to, at a time subsequent to acquisition of said magnetic resonance data representing said first phase image, operate said magnetic resonance scanner to acquire magnetic resonance data from the examination subject in the magnetic resonance scanner representing a second phase image and to contemporaneously acquire magnetic resonance data from the phantom representing a second reference phase image; and a computer configured to generate a temperature map of the examination subject from said first and second phase images, said computer also being configured to identify adaptations of said first and second reference phase images relative to each other that are necessary to calibrate said first and second reference phase images, and to adapt said first and second phase images relative to each other according to said adaptations.

* * * * *